United States Patent [19]

Abts

[11] 4,398,424

[45] Aug. 16, 1983

[54] ULTRASONIC SENSING

[75] Inventor: Leigh R. Abts, Providence, R.I.

[73] Assignee: Micro Pure Systems, Inc., Smithfield, R.I.

[21] Appl. No.: 217,088

[22] Filed: Dec. 16, 1980

[51] Int. Cl.³ ............................................. G01N 29/00
[52] U.S. Cl. ..................... 73/632; 73/61 R; 73/644
[58] Field of Search ................ 73/632, 629, 622, 637, 73/638, 644, 19, 861.27, 861.18, 861.25, 61 R; 310/325, 334, 335, 336

[56] References Cited

U.S. PATENT DOCUMENTS

| 2,515,221 | 7/1950 | Henning | 73/861.27 |
|---|---|---|---|
| 3,204,458 | 9/1965 | Gillen | 73/194 |
| 3,751,979 | 8/1973 | Ims | 73/861.27 |
| 3,821,834 | 7/1974 | McElroy | 29/25.35 |
| 3,844,164 | 10/1974 | Romere | 73/637 |
| 3,906,780 | 9/1975 | Baldwin | 73/632 |
| 4,019,373 | 4/1977 | Freeman et al. | 73/644 |
| 4,112,773 | 9/1978 | Abts | 73/642 |
| 4,214,484 | 7/1980 | Abts | 73/61 |

FOREIGN PATENT DOCUMENTS 624390  9/1978  U.S.S.R. ................................ 73/632

Primary Examiner—Stephen A. Kreitman

[57] ABSTRACT

A pulse-echo device with an improved signal-to-noise ratio, in which sound-transmitting material adjacent to the device is coated with a sound-absorbing layer, the layer being sound-impedance matched to the material so that much of the spurious ultrasonic energy travelling in the material passes through the layer-material interface into the layer where it dissipates instead of remaining in the material and reflecting back to the device.

8 Claims, 5 Drawing Figures

ULTRASONIC SENSING

FIELD OF THE INVENTION

This invention relates to obtaining information about flowing fluid streams, for example, the existence of discontinuities in the fluid or the composition of the fluid.

BACKGROUND OF THE INVENTION

The background of this invention pertaining to the detection of discontinuities in a flowing fluid stream is fully set forth in my U.S. Pat. Nos. 4,112,773, and 4,214,484, both hereby incorporated by reference. The background pertaining to obtaining information about the composition of the fluid is set out in my U.S. patent application Ser. No. 136,169, filed Mar. 31, 1980, now abandoned, also hereby incorporated by reference.

It is desirable to increase the signal-to-noise ratio in pulse-echo search units by eliminating spurious acoustic signals which might be detected by the unit. One source of such spurious signals is random sound waves generated by the units themselves, which random waves enter the material adjacent to the unit, and eventually reflect back to the unit thereby interferring with the unit's ability to detect information-carrying signals.

SUMMARY OF THE INVENTION

I have discovered that the signal-to-noise ratio of a pulse-echo device can be improved by coating the sound-transmitting material adjacent to the pulse-echo device with a sound-absorbing layer, which layer is sound-impedance matched to the material whereby ultrasonic energy travelling in the material passes into the sound-absorbing layer where it dissipates instead of returning to the pulse-echo unit.

In preferred embodiments, the sound-absorbing layer is epoxy which is coated around a metal holder for an ultrasonic transmitter-receiver. In another preferred embodiment, the epoxy is coated around the portion of a pipe adjacent to an ultrasonic transmitter-receiver.

PREFERRED EMBODIMENTS

I turn now to the structure and operation of the preferred embodiments, after first briefly describing the drawings.

DRAWINGS

STRUCTURE

Figure 1:
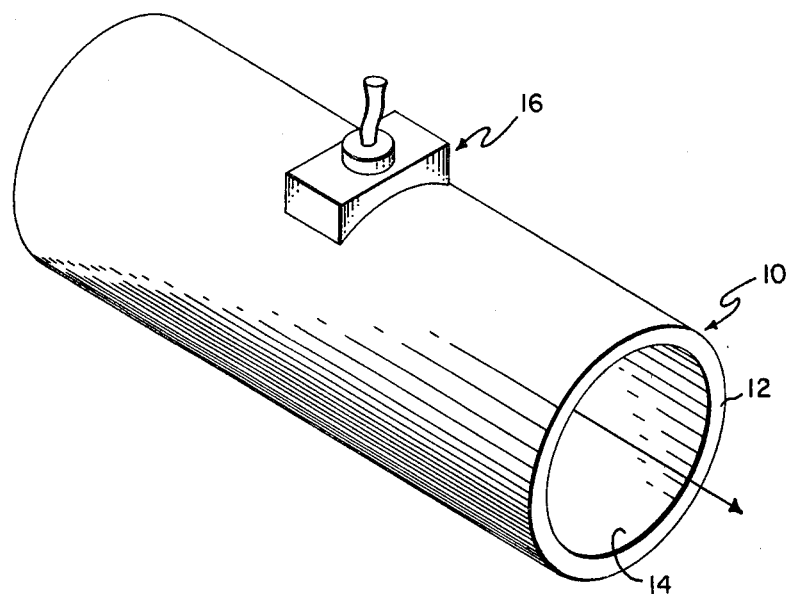
FIG. 1 is a perspective view of the ultrasonic transmitter-receiver of this invention in place on a pipe.

Referring to FIG. 1, there is shown a pipe 10 having a sidewall 12 and an interior bore 14. Ultrasonic transmitter-receiver 16 is mounted on the sidewall 12. Pipe 10 is steel with a 10 inch diameter.

Figure 2:
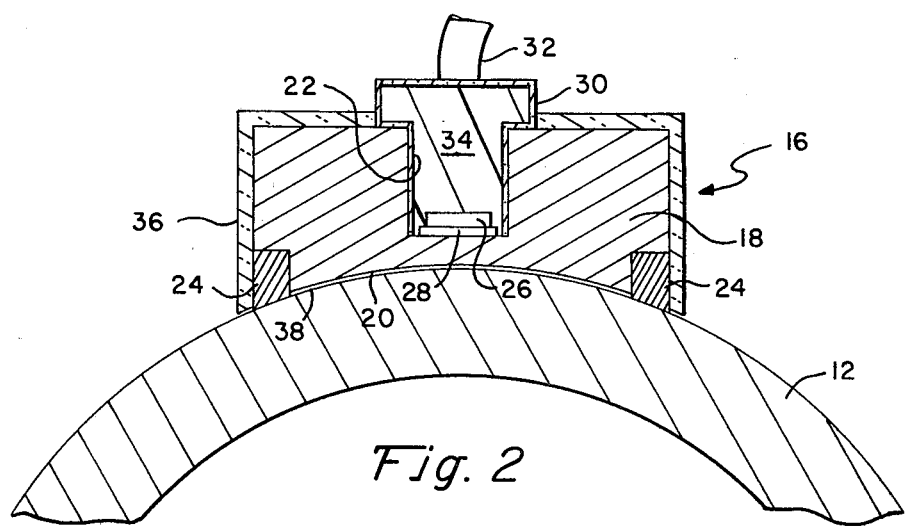
FIG. 2 is an enlarged cross-sectional view of the ultrasonic transmitter-receiver of FIG. 1.

As shown in FIG. 2, ultrasonic transmitter-receiver 16 comprises a holder 18 and a cap 30. Holder 18, which is made of steel, has a concave bottom 20 and a central blind hole 22. The bottom of hole 22 is 0.5 mm above the concave bottom 20. A pair of magnets 24 are disposed on opposite ends of the holder 18 near its concave bottom 22. The magnets 24 each have a five pound pull.

Circular crystal 26 is secured in the bottom of blind hole 22 by a thin layer 28 of epoxy. Crystal 26 is a 3 MHz Lithium Niobate crystal, which is $\frac{1}{2}$ inch in diameter and which has a $\frac{3}{8}$ inch diameter top electrode (not shown). The crystal is available from the Valpey-Fisher Company of Hopkington, Mass. The epoxy is 3M Scotch Weld Structural Adhesive 2214.

Aluminum cap 30 fits into blind hole 22 and covers the crystal 26. Cable 32 is connected to cap 30. The electrial connection of the crystal to the cable 32 (not shown) and an epoxy backing 34 for the crystal are the same as in my U.S. patent application Ser. No. 187,615, filed Sept. 15, 1980, now U.S. Pat. No. 4,365,515, hereby incorporated by reference. The electronic devices to which the cable 32 is connected are preferably those described in my U.S. patent application Ser. No. 136,169, filed Mar. 31, 1980.

After the cap 30 has been put in place, the outside of the holder 18 except for its concave bottom 20 is coated with a layer 36 of epoxy to a depth of about 3 mm. The epoxy, which is 3M Scotch Weld Structural Adhesive 2214, is then cured for 40 minutes at 250° F.

When the epoxy layer 36 has been cured, the area between the concave bottom 20 of the holder and the sidewall 12 of the pipe 10 is covered with stopcock grease to assure proper acoustical coupling, and the ultrasonic transmitter-receiver 16 is then attached to the steel pipe 10 by the magnets 24. If the pipe is non-magnetic, i.e., titanium, a strap or clamp may be used to hold the transmitter-receiver in place.

Operation

The ultrasonic transmitter-receiver 16 is then operated as described in my U.S. patent application Ser. No. 136,169, filed Mar. 31, 1980, with the lenses formed by the concave bottom 20 and the interior curvature of the pipe sidewall 12 focusing the ultrasonic beam across the flow.

Figure 3:
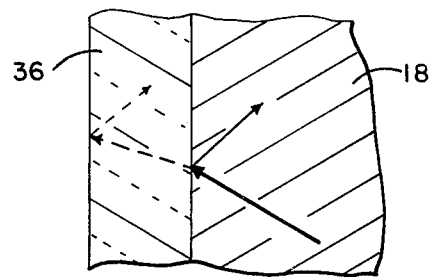
FIG. 3 is an enlarged cross-sectional view of a portion of FIG. 2.

As shown in the enlarged portion of the holder 18 in FIG. 3, stray ultrasonic energy from the crystal 26 (shown by the arrow) travels through the steel holder 18. Because of the poor sound impedance match between metal and air, almost all of this spurious sound would be reflected back into the metal when it hit a holder-air interface, and eventually it would return to the crystal 16 where it would make the detected, information-carrying signal very noisy. However, the epoxy layer 36 has a much closer sound-impedance match with holder 18, and thus, as shown in FIG. 3, the majority of a stray sound signal in the holder 18 passes into the layer 36 rather than reflect at the layer-holder interface. As the epoxy layer 36 is sound-absorbtive and of a substantial thickness, most of the signal which enters the layer dissipates before it can return to the holder 18. Therefore, very little of the spurious signals return to the crystal, and the signal-to-noise ratio is improved.

OTHER EMBODIMENTS

Figure 4:
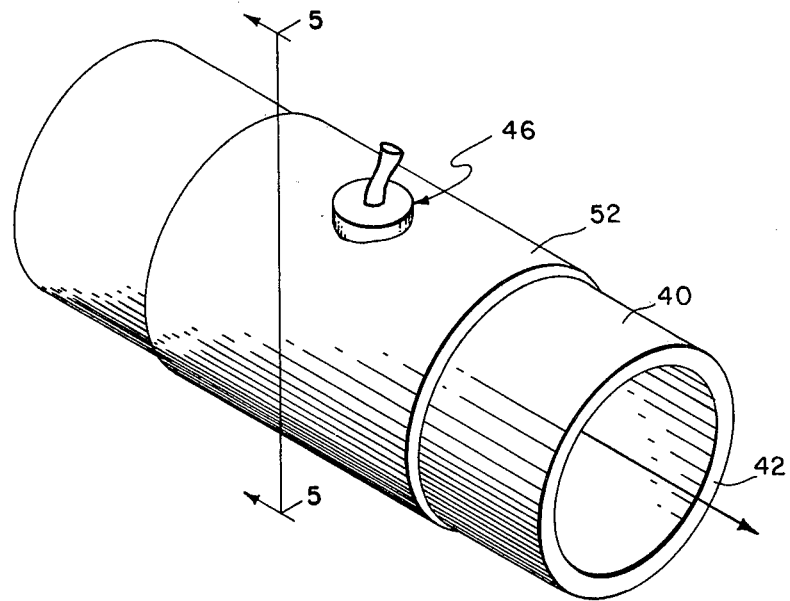
FIG. 4 is a perspective view of another ultrasonic transmitter-receiver on a pipe.
Figure 5:
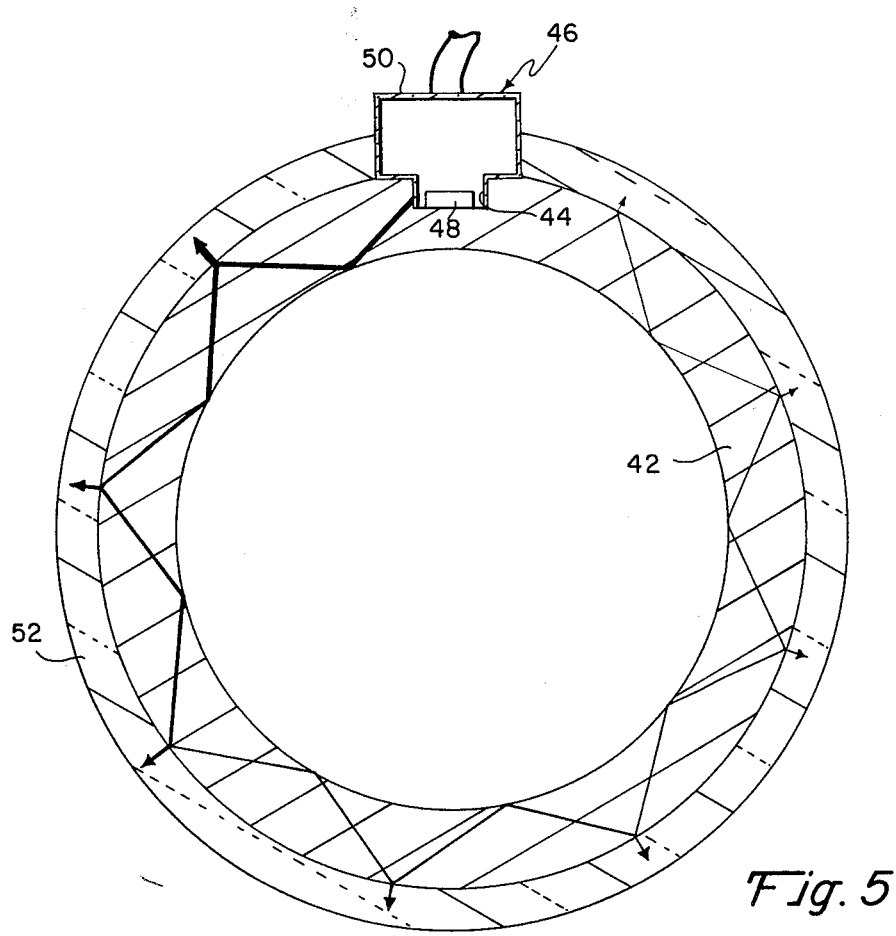
FIG. 5 is an enlarged cross-sectional view of the ultrasonic transmitter-receiver and pipe of FIG. 4.

As shown in FIGS. 4 and 5, a pipe 40, which is $\frac{1}{2}$ inch in diameter and made of titanium, has a sidewall 42 with a blind hole 44. Ultrasonic transmitter-receiver 46 is mounted in the blind hole 44. The transmitter-receiver 46 comprises a crystal 48 fastened to the bottom of the hole 44 in the same manner as the previous embodiment and a cap 50 connected as in the previous embodiment.

The crystal 48 is a 10 MHz Lithium Niobate crystal with a ¼ inch diameter and a 0.04 inch diameter upper electrode (not shown). This smaller crystal is used for the smaller pipe applications. The blind hole 44 may be drilled directly in the sidewall 42 of the pipe 40 instead of using the holder of the previous embodiment when the flow through the pipe is not too hot or under too much pressure. An epoxy layer 52 of the same type as the previous embodiment surrounds the pipe 40. The layer 52 is about 3 mm thick.

In operation stray signals (shown by the arrows) from the crystal 48 enter the sidewall 42 of the pipe 40. Ordinarily, because of the metal-air interface, as previously explained, the signal would remain in the sidewall 42 and travel transversely around the pipe 12 until it returned to the crystal 42 with almost the same strength as when it left. Depending upon a number of factors including the nature of the flow and the time between bursts of ultrasonic energy from the crystal, with the smaller ½ inch diameter pipe, the spurious signal would return to the crystal 48 in time to interfere with the returning echo from the flow. With the larger 10 inch diameter pipe of the preferred embodiment, this spurious signal would return too late to interfere and thus it is not necessary to apply a layer around the larger pipe under normal operating conditions. Accordingly, as shown in FIG. 5, the layer of epoxy 52 absorbs some of the signal each time it strikes the epoxy-pipe interface, until by the time the signal has circled the pipe, very little is left to reenter the crystal.

It should be appreciated that throughout this application the term sound impedance matching is used in a general sense only, and it does not imply an exact match between the materials and the epoxy layer.

Other embodiments of the invention will occur to those skilled in the art.

What is claimed is:

1. A pulse-echo device which uses low intensity signals for obtaining information about very small particulates in a fluid flowing through a pipe comprising:
   a transducer for producing low intensity energy waves,
      said transducer in order to reduce energy wave losses so as to enable the small particulates to be detected being in direct acoustical contact with the pipe which is comprised of a sound-transmitting material,
   a sound-absorbing layer coating said pipe material,
      said layer being sound-impedance matched to said pipe material so that most of any spurious sound waves travelling in said pipe material pass into said layer where they dissipate.

2. The device of claim 1 wherein said layer is epoxy and said material is metal.

3. The device of claim 2 wherein said epoxy layer is cured at 250° F. after it is applied to said material.

4. The device of claim 2 wherein said layer is 3 mm thick.

5. The device of claim 1 wherein said transducer has a holder, said holder being made of a sound-transmitting material and being in sound communication with said transducer.

6. The device of claim 5 wherein said holder has a blind hole in which said transducer is mounted, said holder being adapted to be connected to the pipe.

7. The device of claim 6 wherein said holder has a concave bottom adapted to fit on the sidewall of a pipe.

8. The device of claim 6 wherein said holder has at least one magnet for attaching said holder to a metal pipe.

* * * * *